US006361788B1

(12) United States Patent
Antoni-Zimmermann et al.

(10) Patent No.: US 6,361,788 B1
(45) Date of Patent: Mar. 26, 2002

(54) SYNERGISTIC BIOCIDE COMPOSITION

(75) Inventors: Dagmar Antoni-Zimmermann, Speyer; Rüdiger Baum, Waghäusel; Thomas Wunder, Neustadt/Wstr.; Hans-Jürgen Schmidt, Speyer, all of (DE)

(73) Assignee: Thor Chemie GmbH, Speyer (DE)

( * ) Notice: Subject to any disclaimer, the term of this patent is extended or adjusted under 35 U.S.C. 154(b) by 0 days.

(21) Appl. No.: 09/485,975

(22) PCT Filed: Aug. 20, 1998

(86) PCT No.: PCT/EP98/05310

§ 371 Date: Feb. 18, 2000

§ 102(e) Date: Feb. 18, 2000

(87) PCT Pub. No.: WO99/08530

PCT Pub. Date: Feb. 25, 1999

(30) Foreign Application Priority Data

Aug. 20, 1997 (EP) ............................................. 97114397

(51) Int. Cl.⁷ ............................................... A01N 25/32

(52) U.S. Cl. ........................ 424/406; 424/405; 514/372; 514/373

(58) Field of Search ................................. 424/405, 406; 514/937, 938, 372, 373

(56) References Cited

FOREIGN PATENT DOCUMENTS

| EP | 0363011 | * | 4/1990 |
| JP | 1224306 | * | 9/1989 |

* cited by examiner

*Primary Examiner*—Neil S. Levy
(74) *Attorney, Agent, or Firm*—Hedman & Costigan, P.C.

(57) ABSTRACT

A biocide composition is provided as an addition to substances that can be infected by harmful microorganisms, in which the biocide composition has at least two active biocidal substances, one of which is 2-methylisothiazolin-3-one. The composition is characterized in that it contains 1,2-benzisothiazolin-3-one, compositions containing 5-chloro-2-methylisothiazolin-3-one being excluded. In comparison with its individual components, the composition of the invention has a synergistic biocidal activity.

18 Claims, No Drawings

SYNERGISTIC BIOCIDE COMPOSITION

This application is a 371 of PCT/EP98/05310 Aug. 20, 1998.

The invention relates to a biocide composition as an addition to substances that can be infected by harmful microorganisms. In particular the invention concerns a biocide composition having at least two active biocidal substances that interact synergistically, in which one of the active substances is 2-methylisothiazolin-3-one.

Biocidal agents are used in many fields, for example, to control harmful bacteria, fungi, or algae. The use of 4-isothiazolin-3-ones (which are also designated as 3-isothiazolones) in such compositions has been known for a long time, since these include very effective biocidal compounds.

One of these compounds is 5-chloro-2-methylisothiazolin-3-one. Whereas it does indeed exhibit good biocidal activity, there are various disadvantages when it is handled in practice. For example, the compound frequently triggers allergies in persons that use it. Also, there are legal restrictions in many countries on the AOX value of industrial waste waters, i.e., a certain concentration of organic chlorine, bromine, and iodine compounds that can adsorb to activated carbon must not be exceeded in the water. This prevents the use of 5-chloro-2-methylisothiazolin-3-one to the desired extent. Furthermore, the stability of this compound is inadequate in certain circumstances, e.g., at high pH values or in the presence of nucleophiles or reducing agents.

Another known isothiazolin-3-one with biocidal activity is 2-methylisothiazolin-3-one. While it is true that the compound avoids various disadvantages of 5-chloro-2-methylisothiazolin-3-one, for example, the high risk of allergy, its biocidal activity is considerably lower. Thus, a simple substitution of 2-methylisothiazolin-3-one for 5-chloro-2-methylisothiazolin-3-one is not possible.

The use of combinations of various isothiazolin-3-ones or combinations of at least one isothiazolin-3-one and other compounds is also already known. For example, a synergistic biocidal composition that contains 2-methylisothiazolin-3-one (2-methyl-3-isothiazolone) and 2-n-octylisothiazolin-3-one (2-n-octyl-3-isothiazolone) is described in EP 0676140 A1.

Synergistic biocide compositions that are combinations of 1,2-benzisothiazolin-3-one and an iodopropargyl compound (iodopropinyl compound) are known from U.S. Pat. No. 5,328,926. For example, 3-Iodopropargyl-N-butyl carbamate is named as such a compound. In the said document, however, no biocide compositions are described that contain further active biocidal substances besides 1,2-benzisothiazolin-3-one and 3-iodopropargyl-N-butyl carbamate.

In JP 01224306 (Chemical Abstracts, Vol. 112, Nos. 11, Mar. 12, 1990, Abstract No. 93924), a biocide composition is described that consists of 2-methylisothiazolin-3-one, 1,2-benzisothiazolin-3-one, and 5-chloro-2-methylisothiazolin-3-one.

JP 06092806 (Chemical Abstracts, Vol. 121, Nos. 11, Sep. 12, 1994, Abstract No. 127844) relates to biocide compositions that contain an isothiazolinone, 1,2-benzisothiazolin-3-one, and propanol or a propanol derivative. 2-Methylisothiazolin-3-one is named, for example, as the isothiazolinone and 2-bromo-2-nitropropane-1,3-diol, for example, as the propanol derivative. However, no reference is made to a composition that specifically contains 2-methylisothiazolin-3-one, 1,2-benzisothiazolin-3-one, and 2-bromo-2-nitropropane-1,3-diol and is simultaneously free of 5-chloro-2-methylisothiazolin-3-one.

The object of the invention is to provide a biocide composition that is improved in that its components interact synergistically and therefore can be used in lower concentrations when used simultaneously, compared to the concentrations necessary in the case of the individual components. Thus, humans and the environment are exposed to less pollution and the costs of controlling harmful microorganisms are reduced.

This object is achieved by the invention by means of a biocide composition having at least two active biocidal substances, one of which is 2-methylisothiazolin-3-one. The composition is characterized in that it contains as a further active biocidal substance 1,2-benzisothiazolin-3-one, biocide compositions containing 5-chloro-2-methylisothiazolin-3-one, being excluded.

The biocide composition of the invention has the advantage that it can replace active substances used until now in practice, but suffering from disadvantages with respect to health and the environment, e.g., 5-chloro-2-methylisothiazolin-3-one. Moreover, the biocide composition of the invention can be produced with water as a favorable medium, if necessary. The addition of emulsifiers, organic solvents, and/or stabilizers is thus not necessary. Moreover the invention makes it possible to match the composition to specific goals by adding further active substances, for example, in the sense of an increased biocidal activity, improved long-term protection of the substances infected by microorganisms, improved compatibility with the substances to be protected, or improved toxicological or ecotoxicological behavior.

The biocide composition of the invention contains 2-methylisothiazolin-3-one and 1,2-benzisothiazolin-3-one, normally in a weight ratio of (50–1): (1–50), preferably in a weight ratio of (15–1): (1–8), in particular in a weight ratio of (4–1) (1–4). A weight ratio of 1:1 is particularly preferred.

In the biocide composition the 2-methylisothiazolin-3-one and the 1,2-benzisothiazolin-3-one are present in a total concentration of preferably 0.5 to 50% by wt, in particular 1 to 20% by wt, particularly preferred 2.5 to 10% by wt, in each case relative to the total biocide composition.

It is advisable to use the biocides of the composition of the invention in combination with a polar or nonpolar liquid medium. This medium can be supplied, for example, in the biocide composition and/or in the substance to be preserved.

Preferred polar liquid media are water, an aliphatic alcohol having 1 to 4 carbon atoms, e.g., ethanol and isopropanol, a glycol, e.g., ethylene glycol, diethylene glycol, 1,2-propylene glycol, dipropylene glycol, and tripropylene glycol, a glycol ether, e.g., butyl glycol and butyl diglycol, a glycol ester, e.g., butyl diglycol acetate or 2,2,4-trimethylpentanediol monoisobutyrate, a polyethylene glycol, a polypropylene glycol, N,N-dimethylformnamide, or a mixture of such substances. The polar liquid medium is in particular water, where the pH value of the corresponding biocide composition is preferably adjusted to be neutral or weakly alkaline, for example, to a pH value of 7 to 9. Thus, the 2-methylisothiazolin-3-one is then present in dissolved form and the 1,2-benzisothiazolin-3-one is present in finely dispersed form, or both active substances are dissolved.

For example, aromatics, preferably xylene and toluene, serve as nonpolar liquid media.

The biocide composition of the invention can also be combined simultaneously with a polar and a nonpolar liquid medium.

In addition to 2-methylisothiazolin-3-one and 1,2-benzisothiazolin-3-one, the biocide composition of the invention can contain one or more other active biocidal substances, selected in accordance with the field of application. Specific examples of such additional active biocidal substances are shown below:

benzyl alcohol
2,4-dichlorobenzyl alcohol
2-phenoxyethanol
2-phenoxyethanol hemiformal
phenylethyl alcohol
5-bromo-5-nitro- 1,3-dioxane
formaldehyde and formaldehyde source materials
dimethyloldimethyl hydantoin
glyoxal
glutardialdehyde
sorbic acid
benzoic acid
salicylic acid
p-hydroxybenzoic acid ester
chloroacetamide
N-methylolchloroacetamide
phenols, such as p-chloro-m-cresol and o-phenylphenol
N-methylolurea
N,N'-dimethylolurea
benzyl formal
4,4-dimethyl- 1,3-oxazolidine
1,3,5-hexahydrotriazine derivatives
quaternary ammonium compounds, such as
   N-alkyl-N,N-dimethylbenzyl ammonium chloride and
   di-n-decyldimethyl ammonium chloride
cetylpyridinium chloride
diguanidine
polybiguanide
chlorohexidine
1,2-dibromo-2,4-dicyanobutane
3,5-dichloro4-hydroxybenzaldehyde
ethylene glycol hemiformal
tetra(hydroxymethyl)phosphonium salts
dichlorophen
2,2-dibromo-3-nitrilopropionic acid amide
3-iodo-2-propinyl-N-butyl carbamate
methyl-N-benzimidazol-2-yl carbamate
2-n-octylisothiazolin-3-one
4, 5-dichloro-2-n-octylisothiazolin-3-one
4,5-trimethylene-2-methylisothiazolin-3 -one
2,2'-dithiodibenzoic acid di-N-methylamide
benzisothiazolinone derivatives
2-thiocyanomethylthiobenzothiazole
C formals, such as
   2-hydroxymethyl-2-nitro- 1,3-propanediol
   2-bromo-2-nitropropane- 1,3-diol
methylene bisthiocyanate
reaction products of allantoin 3-Iodo-2-propinyl-N-butyl carbamate, 2-n-octylisothiazolin-3-one, formaldehyde or a formaldehyde source material, and 2-bromo-2-nitropropane-1,3-diol are preferred as such other active biocidal substances.

Examples of the formaldehyde source material are N-formals such as
   N,N'-dimethylolurea
   N-methylolurea
   dimethyloldimethyl hydantoin
   N-methylolchloroacetamide
   reaction products of allantoin
glycol formals such as
   ethylene glycol formal
   butyl diglycol formal
   benzyl formal The biocide composition of the invention can also contain other customary constituents known as additives to those skilled in the art in the field of biocides. These are, e.g., thickening agents, defoaming agents, substances to adjust the pH value, perfumes, dispersing agents, and coloring substances.

2-Methylisothiazolin-3-one and 1,2-benzisothiazolin-3-one are known substances. 2-Methylisothiazolin-3-one can be produced, for example, according to U.S. Pat. No. 5,466,818. The reaction product obtained thereby can be purified, e.g., by column chromatography.

1,2-Benzisothiazolin-3-one is commercially available, for example, under the trade name Acticide® BW 20 and Acticide® BIT from the company Thor Chemie GmbH.

3-Iodo-2-propinyl-N-butyl carbamate is likewise commercially available, for example, from the Troy Chemical Company under the trade name Polyphase®, Polyphase® AF-1, and Polyphase® NP-1, or from Olin Corporation under the trade name Omacide® IPBC 100.

2-n-Octylisothiazolin-3-one is also commercially available, for example, from the company Thor Chemie GmbH under the trade name Acticide® OIT.

Finally 2-bromo-2-nitropropane-1,3-diol is commercially available, for example, from the company Boots under the trade name Myacide® AS.

According to a first embodiment of the invention, the biocide composition of the invention is a system in which the combination of 2-methylisothiazolin-3-one and 1,2-benzisothiazolin-3-one synergistically develops a biocidal activity greater than that exhibited by each of these compounds alone.

Also, in so far as the biocide composition of the invention according to further embodiments of the invention contains, in addition to the two-component combination of 2-methylisothiazolin-3-one and 1,2-benzisothiazolin-3-one, one of the further active biocidal substances 3-iodo-2-propinyl-N-butyl carbamate, 2-n-octylisothiazolin-3-one, formaldehyde or formaldehyde source material, or 2-bromo-2-nitropropane-1,3-diol, a synergistic biocidal activity is achieved greater than that exhibited by the above-mentioned two-component combination and each of these further active substances alone.

When the two-component combination is used together with one of the above-mentioned further active biocidal substances, it contains 2-methylisothiazolin-3-one and 1,2-benzisothiazolin-3-one, preferably in a weight ratio of 1:1. Any other weight ratio can also be selected, however, in so far as a synergistic activity is achieved thereby.

The biocide composition of the invention can be used in very different fields. It is suitable, for example, for use in paints, plasters, lignosulfonates, chalk suspensions, adhesives, photochemicals, casein-containing products, starch-containing products, bituminous emulsions, surfactant solutions, motor fuels, cleaning agents, cosmetic products, water circulating systems, polymer dispersions, and cooling lubricants, against attack by, for example, bacteria, filamentous fungi, yeasts, and algae.

In practice, the biocide composition can be used either as a ready-to-use mixture or by adding the biocides and the remaining components of the composition separately to the substance to be preserved.

The examples illustrate the invention.

In all the examples in which an active substance mixture of MIT and BIT as well as additionally a further active biocidal substance was used, the weight ratio of MIT to BIT was 1:1.

EXAMPLE 1

This example shows the synergy of the two essential active substances in the biocide composition of the invention.

For this purpose, aqueous mixtures were produced with various concentrations of 2-methylisothiazolin-3-one (MIT) and 1,2-benzisothiazolin-3-one (BIT) and the activity of these mixtures on *Escherichia coli* (International Mycological Institute, Strain No. IMI 362054) was tested.

In addition to the biocide component and water, the aqueous mixtures contained a nutrient medium, namely a Müller-Hinton broth (commercial product "Merck No. 10393"). The cell density of *Escherichia coli* was $10^6$ cells/mL. The incubation time was 72 h at 25° C. Each sample was incubated on an incubation shaker at 120 rpm.

Table 1 below shows the concentrations of MIT and BIT used. The table also shows whether growth of the microorganism took place (symbol "+") or not (symbol "−").

Thus, table 1 also shows the minimum inhibition concentrations (MIC). According to this, an MIC value of 17.5 ppm is found when MIT is used alone and an MIC value of 25 ppm when BIT is used alone. In contrast, the MIC values of mixtures of MIT and BIT are clearly lower, i.e., when they are combined, MIT and BIT act synergistically.

II. The synergy index is calculated according to the method of F. C. Kull et al., Applied Microbiology, Vol. 9 (1961), p. 538. Here the synergy index is calculated using the following formula:

$$\text{Synergy index } SI = Q_a/Q_A + Q_b/Q_B.$$

When this formula is used on the biocide system tested here, the quantities in the formula have the following meaning:

$Q_a$=concentration of BIT in the biocide mixture of BIT and MIT $Q_A$=concentration of BIT as sole biocide $Q_b$=concentration of MIT in the biocide mixture of MIT and BIT $Q_B$=concentration of MIT as sole biocide When the synergy index exhibits a value greater than 1, this means that there is an antagonism. When the synergy index has the value 1, this means that there is an addition of the activity of the two biocides. When the synergy index has a value of less than 1, this means that a synergy of the two biocides exists.

TABLE I

MIC values for *Escherichia coli* at an incubation time of 72 h

| MIT concentration (ppm) | BIT concentration (ppm) | | | | | | | | | | | |
|---|---|---|---|---|---|---|---|---|---|---|---|---|
| | 35 | 30 | 25 | 20 | 17.5 | 15 | 12.5 | 10 | 7.5 | 5 | 2.5 | 1 | 0 |
| 25   | − | − | − | − | − | − | − | − | − | − | − | − | − |
| 17.5 | − | − | − | − | − | − | − | − | − | − | − | − | − |
| 15   | − | − | − | − | − | − | − | − | − | − | − | − | + |
| 12.5 | − | − | − | − | − | − | − | − | − | − | − | + | + |
| 10   | − | − | − | − | − | − | − | − | − | − | − | + | + |
| 7.5  | − | − | − | − | − | − | − | − | − | + | + | + | + |
| 5    | − | − | − | − | − | − | − | + | + | + | + | + | + |
| 2.5  | − | − | − | − | + | + | + | + | + | + | + | + | + |
| 1    | − | − | − | + | + | + | + | + | + | + | + | + | + |
| 0    | − | − | − | + | + | + | + | + | + | + | + | + | + |

The synergy that occurs is represented numerically by means of the calculation of the synergy index given in Table

TABLE II

Calculation of the synergy index for *Escherichia coli* at an incubation time of 72 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 0    | 17.5 | 17.5 | 0.0  | 100.0 | 0.00 | 1.00 | 1.00 |
| 1    | 15   | 16   | 6.3  | 93.8  | 0.04 | 0.86 | 0.90 |
| 2.5  | 10   | 12.5 | 20.0 | 80.0  | 0.10 | 0.57 | 0.67 |
| 7.5  | 7.5  | 15   | 50.0 | 50.0  | 0.30 | 0.43 | 0.73 |
| 12.5 | 5    | 17.5 | 71.4 | 28.6  | 0.50 | 0.29 | 0.79 |

TABLE II-continued

Calculation of the synergy index for *Escherichia coli* at an incubation time of 72 h

| MIC at BIT concentration $Q_a$ (ppm) | MIC at MIT concentration $Q_b$ (ppm) | Total concentration BIT + MIT $Q_a + Q_b$ (ppm) | Concentration BIT (% by wt) | Concentration MIT (% by wt) | $Q_a/Q_A$ | $Q_b/Q_B$ | Synergy index $Q_a/Q_A + Q_b/Q_B$ |
|---|---|---|---|---|---|---|---|
| 20 | 2.5 | 22.5 | 88.9 | 11.1 | 0.80 | 0.14 | 0.94 |
| 25 | 0 | 25 | 100.0 | 0.0 | 1.00 | 0.00 | 1.00 |

It can be seen from Table II that the optimum synergy, i.e., the lowest synergy index (0.67) of an MIT/BIT mixture, is at a mixture of 80% by wt of MIT and 20% by wt of BIT.

EXAMPLE 2

The synergy of the two active substances MIT and BIT against the microorganism *Pseudomonas putida* is shown as in Example 1.

The test batches again contained a Müller-Hinton broth as a nutrient medium. The cell density was $10^6$ cells/mL. The incubation time was 48 h at 25° C. Each sample was incubated on an incubation shaker at 120 rpm.

Table III below shows the MIC values of the tested biocide compositions. The MIC value was 12.5 ppm when MIT alone was used, and 60 ppm when BIT alone was used.

With the simultaneous use of MIT and BIT a synergy occurred. Table IV shows the calculation of the synergy index. According to this, for *Pseudomonas putida* the lowest synergy index (0.50) was at a mixture of 3.8% by wt of MIT and 96.2% by wt of BIT.

TABLE III

MIC values for *Pseudomonas putida* at an incubation time of 48 h

| MIT concentration (ppm) | BIT concentration (ppm) |||||||||||||||
|---|---|---|---|---|---|---|---|---|---|---|---|---|---|---|---|
| | 80 | 70 | 60 | 50 | 40 | 30 | 25 | 20 | 15 | 10 | 7.5 | 5 | 2.5 | 1 | 0.5 | 0 |
| 17.5 | − | − | − | − | − | − | + | − | − | − | − | − | − | − | − | − |
| 12.5 | − | − | − | − | − | − | − | − | − | − | − | − | − | − | − | − |
| 10 | − | − | − | − | − | − | − | − | − | − | − | − | − | + | + | + |
| 7.5 | − | − | − | − | − | − | − | − | − | − | − | − | + | + | + | + |
| 5 | − | − | − | − | − | − | − | − | − | + | + | + | + | + | + | + |
| 2.5 | − | − | − | − | − | − | − | − | + | + | + | + | + | + | + | + |
| 1 | − | − | − | − | − | − | − | + | + | + | + | + | + | + | + | + |
| 0.5 | − | − | − | − | − | + | + | + | + | + | + | + | + | + | + | + |
| 0 | − | − | − | + | + | + | + | + | + | + | + | + | + | + | + | + |

TABLE IV

Calculation of the synergy index for *Pseudomonas putida* at an incubation time of 48 h

| MIC at BIT concentration $Q_a$ (ppm) | MIC at MIT concentration $Q_b$ (ppm) | Total concentration BIT + MIT $Q_a + Q_b$ (ppm) | Concentration BIT (% by wt) | Concentration MIT (% by wt) | $Q_a/Q_A$ | $Q_b/Q_B$ | Synergy index $Q_a/Q_A + Q_b/Q_B$ |
|---|---|---|---|---|---|---|---|
| 0 | 12.5 | 12.5 | 0.0 | 100.0 | 0.00 | 1.00 | 1.00 |
| 2.5 | 10 | 12.5 | 20.0 | 80.0 | 0.04 | 0.80 | 0.84 |
| 5 | 7.5 | 12.5 | 40.0 | 60.0 | 0.08 | 0.60 | 0.68 |
| 15 | 5 | 20 | 75.0 | 25.0 | 0.25 | 0.40 | 0.65 |

TABLE IV-continued

Calculation of the synergy index for *Pseudomonas putida* at an incubation time of 48 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 20 | 2.5 | 22.5 | 88.9 | 11.1 | 0.33 | 0.20 | 0.53 |
| 25 | 1 | 26 | 96.2 | 3.8 | 0.42 | 0.08 | 0.50 |
| 40 | 0.5 | 40.5 | 98.8 | 1.2 | 0.67 | 0.04 | 0.71 |
| 60 | 0 | 60 | 100.0 | 0.0 | 1.00 | 0.00 | 1.00 |

EXAMPLE 3

The synergy of MIT and BIT against the microorganism *Pseudomonas stutzeri* is shown as in Example 1.

The test batches again contained a Müller-Hinton broth as a nutrient medium. The cell density was $10^6$ cells/mL. The incubation time was 72 h at 25° C. Each sample was incubated on an incubation shaker at 120 rpm.

Table V below shows the MIC values of the tested biocide compositions. The MIC value was 12.5 ppm when MIT alone was used, and 20 ppm when BIT alone was used.

With the simultaneous use of MIT and BIT, a synergy occurred. Table VI shows the calculation of the synergy index. According to this, the lowest synergy index (0.65) for *Pseudomonas stutzeri* was at a mixture of 50% by wt of MIT and 50% by wt of BIT.

TABLE V

MIC values for *Pseudomonas stutzeri* at an incubation time of 72 h

| MIT concentration (ppm) | BIT concentration (ppm) | | | | | | | | | |
|---|---|---|---|---|---|---|---|---|---|---|
| | 30 | 25 | 20 | 15 | 10 | 7.5 | 5 | 2.5 | 1 | 0.5 | 0 |
| 30 | | | | | | | | | | | |
| 25 | − | − | − | − | − | − | − | − | − | − | − |
| 20 | − | − | − | − | − | − | − | − | − | − | − |
| 17.5 | − | − | − | − | − | − | − | − | − | − | − |
| 15 | − | − | − | − | − | − | − | − | − | − | − |
| 12.5 | − | − | − | − | − | − | − | − | − | − | − |
| 10 | − | − | − | − | − | − | − | − | − | − | + |
| 7.5 | − | − | − | − | − | − | − | + | + | + | + |
| 5 | − | − | − | − | − | − | − | + | + | + | + |
| 2.5 | − | − | − | − | − | + | + | + | + | + | + |
| 1 | − | − | − | − | + | + | + | + | + | + | + |
| 0.5 | − | − | − | + | + | + | + | + | + | + | + |
| 0 | − | − | − | + | + | + | + | + | + | + | + |

TABLE VI

Calculation of the synergy index for *Pseudomonas stutzeri* at an incubation time of 72 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 0 | 12.5 | 12.5 | 0.0 | 100.0 | 0.00 | 1.00 | 1.00 |
| 0.5 | 10 | 10.5 | 4.8 | 95.2 | 0.03 | 0.80 | 0.83 |
| 5 | 5 | 10 | 50.0 | 50.0 | 0.25 | 0.40 | 0.65 |
| 10 | 2.5 | 12.5 | 80.0 | 20.0 | 0.50 | 0.20 | 0.70 |
| 15 | 1 | 16 | 93.8 | 6.3 | 0.75 | 0.08 | 0.83 |

TABLE VI-continued

Calculation of the synergy index for *Pseudomonas stutzeri* at an incubation time of 72 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 20 | 0 | 20 | 100.0 | 0.0 | 1.00 | 0.00 | 1.00 |

EXAMPLE 4

The synergy of the two active substances MIT and BIT against the microorganism *Klebsiella pneumoniae* is shown as in example 1.

The test batches again contained a Müller-Hinton broth as a nutrient medium. The cell density was $10^6$ cells/mL. The incubation time was 72 h at 25° C. Each sample was incubated on an incubation shaker at 120 rpm.

Table VII below shows the MIC values of the tested biocide compositions. The MIC value was 20 ppm when MIT alone was used, and 25 ppm when BIT alone was used.

With the simultaneous use of MIT and BIT, a synergy occurred. Table VIII shows the calculation of the synergy index. According to this, the lowest synergy index (0.68) for *Pseudomonas aeruginosa* [sic] was at a mixture of 50% by wt of MIT and 50% by wt of BIT.

TABLE VII

MIC values for *Klebsiella pneumoniae* at an incubation time of 72 h

| MIT concentration (ppm) | BIT concentration (ppm) | | | | | | | | | |
|---|---|---|---|---|---|---|---|---|---|---|
| | 35 | 30 | 25 | 20 | 15 | 10 | 7.5 | 5 | 2.5 | 1 | 0 |
| 25 | − | − | − | − | − | − | − | − | − | − | − |
| 20 | − | − | − | − | − | − | − | − | − | − | − |
| 17.5 | − | − | − | − | − | − | − | − | − | + | + |
| 15 | − | − | − | − | − | − | − | − | − | + | + |
| 12.5 | − | − | − | − | − | − | − | − | − | + | + |
| 10 | − | − | − | − | − | − | − | − | + | + | + |
| 7.5 | − | − | − | − | − | − | − | + | + | + | + |
| 5 | − | − | − | − | − | + | + | + | + | + | + |
| 2.5 | − | − | − | + | + | + | + | + | + | + | + |
| 1 | − | − | − | + | + | + | + | + | + | + | + |
| 0 | − | − | − | + | + | + | + | + | + | + | + |

TABLE VIII

Calculation of the synergy index for *Klebsiella pneumoniae* at an incubation time of 72 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 0 | 20 | 20 | 0.0 | 100.0 | 0.00 | 1.00 | 1.00 |
| 2.5 | 12.5 | 15 | 16.7 | 83.3 | 0.10 | 0.63 | 0.73 |
| 5 | 10 | 15 | 33.3 | 66.7 | 0.20 | 0.50 | 0.70 |
| 7.5 | 7.5 | 15 | 50.0 | 50.0 | 0.30 | 0338 | 0.68 |
| 15 | 5 | 20 | 75.0 | 25.0 | 0.60 | 0.25 | 0.85 |
| 25 | 0 | 25 | 100.0 | 0.0 | 1.00 | 0.00 | 1.00 |

EXAMPLE 5

The synergy of the two active substances MIT and BIT against the microorganism *Pseudomonas aeruginosa* is shown as in Example 1.

The test batches again contained a Müller-Hinton broth as a nutrient medium. The cell density was $10^6$ cells/mL. The incubation time was 48 h at 25° C. Each sample was incubated on an incubation shaker at 120 rpm.

Table IX below shows the MIC values of the tested biocide compositions. The MIC value was 30 ppm when MIT alone was used, and 150 ppm when BIT alone was used.

TABLE IX

MIC values for *Pseudomonas aeruginosa* at an incubation time of 48 h

| MIT concentration | BIT concentration (ppm) | | | | | | | | | |
|---|---|---|---|---|---|---|---|---|---|---|
| (ppm) | 200 | 175 | 150 | 125 | 100 | 75 | 50 | 25 | 10 | 5 | 0 |
| 50 | − | − | − | − | − | − | − | − | − | − | − |
| 40 | − | − | − | − | − | − | − | − | − | − | − |
| 30 | − | − | − | − | − | − | − | − | − | − | − |
| 20 | − | − | − | − | − | − | − | − | − | + | + |
| 10 | − | − | − | − | − | − | + | + | + | + |
| 5 | − | − | − | − | − | + | + | + | + | + | + |
| 2.5 | − | − | − | − | + | + | + | + | + | + | + |
| 1 | − | − | − | + | + | + | + | + | + | + | + |
| 0 | − | − | − | + | + | + | + | + | + | + | + |

With the simultaneous use of MIT and BIT, a synergy occurred. Table X shows the calculation of the synergy index. According to this, the lowest synergy index (0.67) for *Pseudomonas aeruginosa* was at a mixture of 16.7% by wt of MIT and 83.3% by wt of BIT.

TABLE X

Calculation of the synergy index for *Pseudomonas aeruginosa* at an incubation time of 48 h

| MIC at | | Total concentration | Concentration | | | | Synergy index |
|---|---|---|---|---|---|---|---|
| BIT | MIT | BIT + MIT | | | | | |
| concentration $Q_a$ (ppm) | concentration $Q_b$ (ppm) | $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 0 | 30 | 30 | 0.0 | 100.0 | 0.00 | 1.00 | 1.00 |
| 10 | 20 | 30 | 33.3 | 66.7 | 0.07 | 0.67 | 0.73 |
| 50 | 10 | 60 | 83.3 | 16.7 | 0.33 | 0.33 | 0.67 |
| 100 | 5 | 105 | 95.2 | 4.8 | 0.67 | 0.17 | 0.83 |
| 125 | 2.5 | 127.5 | 98.0 | 2.0 | 0.83 | 0.08 | 0.92 |
| 150 | 0 | 150 | 100.0 | 0.0 | 1.00 | 0.00 | 1.00 |

EXAMPLE 6

A biocide composition of the following components was produced:

| Component | Amount (% by wt) |
|---|---|
| 2-Methylisothiazolin-3-one (98% by wt) | 5.1 |
| 1,2-Benzisothiazolin-3-one (in the form of a mixture of 74.6% by wt of BIT and 25.4% by wt of water; commercial product "Acticide ® BIT" of the company Thor Chemie GmbH) | 6.7 |
| Polyethylene glycol (average molar weight 400 g/mol) | 88.2 |
| | 100.0 |

The ready-to-use formulation of the biocide composition is a clear solution, which can be attributed to the polyethylene glycol. The solution is suitable for use, e.g., in paints, polymer dispersions, plaster systems, and cooling lubricants, against attack by bacteria, filamentous fungi and yeasts.

EXAMPLE 7

A biocide composition of the following components was produced:

| Component | Amount (% by wt) |
|---|---|
| 2-Methylisothiazolin-3-one (in the form of a solution of 20% by wt of MIT in water) | 25 |
| 1,2-Benzisothiazolin-3-one | 25 |

-continued

| Component | Amount (% by wt) |
|---|---|
| (in the form of a suspension of 20% by wt of BIT in water; commercial product "Acticide ® BW 20" of the company Thor Chemie GmbH) | |
| Thickener based on xanthan (commercial product "Rhodopol 50 MD" of the company Rhône-Poulenc) | 0.4 |
| Defoaming agent (commercial product "Drewplus T 4202" of the company Drew Ameroid) | 0.1 |
| Water | 49.5 |
| | 100.0 |

In the ready-to-use formulation of the biocide composition, the BIT is present in finely suspended form. The formulation is suitable for the applications given in the specification above.

EXAMPLE 8

A biocide composition of the following components was produced:

| Component | Amount (% by wt) |
|---|---|
| 1,2-Benzisothiazolin-3-one (as a mixture of 74.6% by wt of BIT and 25.4% by wt of water) | 3.35 |
| Water | 92.8 |
| Sodium hydroxide solution (50% by wt in water) | 1.3 |
| 2-Methylisothiazolin-3-one (98% by wt) | 2.55 |
| | 100.0 |

The additional water was added to the BIT/water mixture (weight ratio 74.6:25.4) and then the mixture was converted into a solution by adding the sodium hydroxide solution, which is formed owing to the formation of the corresponding sodium salt. Finally the MIT was added. The ready-to-use formulation was a clear solution and had a pH value of about 8.2.

The ready-to-use formulation of the biocide composition is suitable for the use applications given above.

EXAMPLE 9

Biocide compositions according to the invention were incorporated into a coating composition A that is used for coating building facades. This coating composition is a plaster based on an aqueous polymer dispersion commercially available under the designation "Granol KR 3.0" (company Steinwerke Kupferdreh GmbH). The addition of the biocide composition of the invention served to preserve the coating composition before its use, i.e., while it was stored in its packing drums.

The biocides shown in Table XI below were added respectively to 50 g of coating composition A. The stated amounts of biocide refer to the amount of coating composition A. In the MIT/BIT mixtures, the two biocides were present in a weight ratio of 1:1.

Apart from a blank test without addition of biocide, 1 mL of a standard bacterial inoculum that contained the following bacterial strains was added to each sample of coating composition A:

*Shewanella putrefaciens*
*Alcaligenes faecalis*
*Serratia liquefaciens*
*Klebsiella* species
*Proteus penneri/vulgaris*
*Providencia rettgeri*
*Pseudomonas fluorescens*
*Pseudomonas aeruginosa*
*Pseudomonas stutzeri*
*Escherichia coli*
*Corynebacterium pseudodiphteriae*
*Cellulomonas flavigena*
Corynebacterium species The cell density of the inoculum was $10^{10}$ to $3 \cdot 10^{10}$ cells/mL, and the cell density of the samples was $2 \cdot 10^8$ to $6 \cdot 10^8$ cells/g. The samples were held at 30° C. for 7 days. Then a streak of each sample was produced on a nutrient agar plate, held at 30° C. for 48 h, and then evaluated for bacterial growth. The following evaluation scale was used:

0=no growth
1=minimal growth up to 10 colonies
2=slight growth up to 100 colonies
3=moderate growth up to 300 colonies
4=uniform growth, single colonies still discernible
5 =strong growth, too many colonies to count, but not covering entire surface
6=extensive growth, almost no individual colonies, total streak surface overgrown When the bacterial growth was evaluated as below 6, a second bacterial inoculum of the above-mentioned type was added to the corresponding original 50 g sample and it was again held at 30° C. for 7 days. Then a streak was again produced on a nutrient agar plate, which was again evaluated for its bacterial growth after a holding time of 48 h at 30° C.

When the bacterial growth of the streak was evaluated as 6 for a sample, the testing of this sample was terminated. As long as a sample had not reached this number, a bacterial inoculum was again added in the above-mentioned manner and the sample was held and tested by means of a streak. This procedure was repeated as necessary, with a maximum of 4 bacterial inocula being added per sample.

Table XI summarizes the results for coating composition A.

TABLE XI

| Coating composition A | |
|---|---|
| Biocide (% by wt) | Bacterial growth (7 days + 48 h after 4th inoculation) |
| none | (Growth already after 1st inoculation) |
| BIT 0.005 | (Growth already after 1st inoculation) |
| 0.01 | (Growth already after 1st inoculation) |
| 0.015 | (Growth already after 2nd inoculation) |
| 0.02 | (Growth already after 2nd inoculation) |
| 0.03 | (Growth already after 3rd inoculation) |
| MIT 0.005 | 6 |
| 0.01 | 5 |
| 0.015 | 5 |
| 0.02 | 4 |
| 0.03 | 0 |
| MIT/BIT 0.005 | 5 |

TABLE XI-continued

Coating composition A

| Biocide (% by wt) | Bacterial growth (7 days + 48 h after 4$^{th}$ inoculation) |
|---|---|
| 0.01 | 0 |
| 0.015 | 0 |
| 0.02 | 0 |
| 0.03 | 0 |

It can be seen from Table XI that the sample without addition of biocide developed full bacterial growth already after the first inoculum.

When BIT alone was added, full bacterial growth was reached already after the first inoculation at 0.005% by wt of BIT, after the second inoculation at 0.015% by wt of BIT, and after the third inoculation at 0.03% by wt of BIT.

When MIT alone was added, full bacterial growth was reached only after four inoculations, in fact at the smallest amount of biocide of 0.005% by wt. But a uniform to strong bacterial growth was still found also at the higher biocide concentrations of 0.01, 0.015, and 0.02% by wt of MIT. Only in a sample with the highest concentration of 0.03% by wt of MIT was no bacterial growth found even after four inoculations.

In contrast, the biocide composition of the invention of MIT and BIT proved itself to be considerably more effective. After four inoculations, a distinct bacterial growth occurred only at the lowest concentration of 0.005% by wt of MIT/BIT. Bacterial growth in coating composition A was prevented completely at the higher concentrations in the range of 0.01 to 0.03% by wt of MIT/BIT.

EXAMPLE 10

Example 9 was repeated, but using coating composition B instead of coating composition A.

Coating composition B is a particularly low-emission plaster based on a polymer dispersion commercially available under the designation "Granol KR 3.0 LF" (company Steinwerke Kupferdreh GmbH).

The results using coating composition B are summarized in Table XII below.

TABLE XII

Coating composition B

| Biocide (% by wt) | | Bacterial growth (7 days + 48 h after 4$^{th}$ inoculation) |
|---|---|---|
| none | | (Growth already after 1$^{st}$ inoculation) |
| BIT | 0.005 | (Growth already after 1$^{st}$ inoculation) |
| | 0.01 | (Growth already after #$^{st}$ inoculation) |
| | 0.015 | (Growth already after 2$^{nd}$ inoculation) |
| | 0.02 | (Growth already after 2$^{nd}$ inoculation) |
| | 0.03 | (Growth already after 3$^{rd}$ inoculation) |
| MIT | 0.005 | 4 |
| | 0.01 | 1 |
| | 0.015 | 1 |
| | 0.02 | 0 |
| | 0.03 | 0 |
| MIT/BIT | 0.005 | 5 |
| | 0.01 | 0 |
| | 0.015 | 0 |
| | 0.02 | 0 |
| | 0.03 | 0 |

The results for coating composition B are largely in agreement with those for coating composition A.

Full bacterial growth also took place already after the first inoculation in the case of coating composition B.

When BIT alone was used, complete bacterial attack could be observed after the third inoculation at the latest.

When MIT alone was used, bacterial growth could be prevented completely after the fourth inoculation only with the highest concentrations of 0.02 and 0.03% by wt.

In contrast, it was possible to suppress bacterial growth completely with the MIT/BIT combination according to the invention even at the relatively low concentration of 0.01% by wt.

EXAMPLE 11

The synergy of the two active substances MIT and BIT against the microorganism *Aspergillus niger* is shown as in Example 1.

The test batches contained a Sabouraud maltose broth as a nutrient medium. The spore concentration was 10$^6$ per mL. The incubation time was 96 h at 25° C. Each sample was incubated on an incubation shaker at 120 rpm.

Table XIII below shows the MIC values of the tested biocide compositions. The MIC value was 750 ppm when MIT alone was used, and 100 ppm when BIT alone was used.

TABLE XIII

MIC values for *Aspergillus niger* at an incubation time of 96 h

| MIT concentration (ppm) | BIT concentration (ppm) | | | | | | | |
|---|---|---|---|---|---|---|---|---|
| | 150 | 100 | 75 | 50 | 25 | 10 | 5 | 0 |
| 750 | − | − | − | − | − | − | − | − |
| 500 | − | − | − | − | − | − | + | + |
| 250 | − | − | − | − | − | + | + | + |
| 100 | − | − | − | − | + | + | + | + |
| 75 | − | − | − | + | + | + | + | + |
| 50 | − | − | − | + | + | + | + | + |
| 25 | − | − | − | + | + | + | + | + |
| 10 | − | − | + | + | + | + | + | + |
| 0 | − | − | + | + | + | + | + | + |

With the simultaneous use of MIT and BIT, a synergy occurred. Table XIV shows the calculation of the synergy index. According to this, the lowest synergy index (0.57) for *Aspergillus niger* was at a mixture of 50% by wt of MIT and 50% by wt of BIT.

TABLE XIV

Calculation of the synergy index for *Aspergillus niger* at an incubation time of 96 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 0 | 100 | 100 | 0.0 | 100.0 | 0.00 | 1.00 | 1.00 |
| 25 | 75 | 100 | 25.0 | 75.0 | 0.03 | 0.75 | 0.78 |
| 50 | 75 | 125 | 40.0 | 60.0 | 0.07 | 0.75 | 0.82 |
| 50 | 50 | 100 | 50.0 | 50.0 | 0.07 | 0.50 | 0.57 |
| 75 | 75 | 150 | 50.0 | 50.0 | 0.10 | 0.75 | 0.85 |
| 75 | 50 | 125 | 60.0 | 40.0 | 0.10 | 0.50 | 0.60 |
| 100 | 50 | 150 | 66.7 | 33.3 | 0.13 | 0.50 | 0.63 |
| 250 | 50 | 300 | 83.3 | 16.7 | 0.33 | 0.50 | 0.83 |
| 250 | 25 | 275 | 90.9 | 9.1 | 0.33 | 0.25 | 0.58 |
| 500 | 25 | 525 | 95.2 | 4.8 | 0.67 | 0.25 | 0.92 |
| 500 | 10 | 510 | 98.0 | 2.0 | 0.67 | 0.50 | 0.77 |
| 750 | 0 | 750 | 100.0 | 0.0 | 1.00 | 0.00 | 1.00 |

EXAMPLE 12

The synergy of the two active substances MIT and BIT against the microorganism *Penicillium funiculosum* is shown as in Example 1.

The test batches contained a Sabouraud maltose broth as a nutrient medium. The spore concentration was $10^6$ per mL. The incubation time was 96 h at 25° C. Each sample was incubated on an incubation shaker at 120 rpm.

Table XV below shows the MIC values of the tested biocide compositions. The MIC value was 200 ppm when MIT alone was used, and 40 ppm when BIT alone was used.

TABLE XV

MIC values for *Penicillium funiculosum* at an incubation time of 96 h

| MIT concentration (ppm) | BIT concentration (ppm) | | | | | | | |
|---|---|---|---|---|---|---|---|---|
| | 75 | 50 | 40 | 30 | 20 | 15 | 10 | 0 |
| 200 | − | − | − | − | − | − | − | − |
| 150 | − | − | − | − | − | − | − | + |
| 100 | − | − | − | − | − | − | − | + |
| 75 | − | − | − | − | − | − | + | + |
| 50 | − | − | − | − | − | + | + | + |
| 25 | − | − | − | − | − | + | + | + |
| 10 | − | − | − | − | − | + | + | + |
| 5 | − | − | − | + | + | + | + | + |
| 0 | − | − | − | + | + | + | + | + |

With the simultaneous use of MIT and BIT, a synergy occurred. Table XVI shows the calculation of the synergy index. According to this, the lowest synergy index (0.55) for *Penicillium funiculosum* was at a mixture of 33.3% by wt of MIT and 66.7% by wt of BIT.

TABLE XVI

Calculation of the synergy index for *Penicillium funiculosum* at an incubation time of 96 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 0 | 40 | 40 | 0.0 | 100.0 | 0.00 | 1.00 | 1.00 |
| 10 | 30 | 40 | 25.0 | 75.0 | 0.05 | 0.75 | 0.80 |
| 10 | 20 | 30 | 33.3 | 66.7 | 0.05 | 0.50 | 0.55 |
| 25 | 30 | 55 | 45.5 | 54.5 | 0.13 | 0.75 | 0.88 |
| 25 | 20 | 45 | 55.6 | 44.4 | 0.13 | 0.50 | 0.63 |
| 50 | 20 | 70 | 71.4 | 28.6 | 0.25 | 0.50 | 0.75 |
| 75 | 20 | 95 | 78.9 | 21.1 | 0.38 | 0.50 | 0.88 |
| 75 | 15 | 90 | 83.3 | 16.7 | 0.38 | 0.38 | 0.75 |
| 100 | 15 | 115 | 87.0 | 13.0 | 0.50 | 0.38 | 0.88 |

TABLE XVI-continued

Calculation of the synergy index for *Penicillium funiculosum* at an incubation time of 96 h

| MIC at | | Total concentration | Concentration | | | | Synergy index |
|---|---|---|---|---|---|---|---|
| BIT concentration $Q_a$ (ppm) | MIT concentration $Q_b$ (ppm) | BIT + MIT $Q_a + Q_b$ (ppm) | BIT (% by wt) | MIT (% by wt) | $Q_a/Q_A$ | $Q_b/Q_B$ | $Q_a/Q_A + Q_b/Q_B$ |
| 100 | 10 | 110 | 90.9 | 9.1 | 0.50 | 0.25 | 0.75 |
| 200 | 0 | 200 | 100.0 | 0.0 | 1.00 | 0.00 | 1.00 |

EXAMPLE 13

The synergy of an active substance mixture that contains 3-iodo-2-propinyl-N-butyl carbamate (IPBC) in addition to MIT and BIT, against the microorganism *Aspergillus niger* is shown as in Example 1.

The test batches contained a Sabouraud maltose broth as a nutrient medium. The spore concentration was $10^6$ per mL. The incubation time was 72 h at 25° C. Each sample was incubated on an incubation shaker at 120 rpm.

Table XVII below shows the MIC values of the tested biocide compositions. The MIC value was 150 ppm when MIT/BIT alone was used, and 2.5 ppm when IPBC alone was used.

TABLE XVII

MIC values for *Aspergillus niger* at an incubation time of 72 h

| MIT/BIT concentration (ppm) | IPBC concentration (ppm) | | | | | | | | | |
|---|---|---|---|---|---|---|---|---|---|---|
| | 5 | 4.5 | 4 | 3.5 | 3 | 2.5 | 2 | 1.5 | 1 | 0.75 | 0 |
| 250 | – | – | – | – | – | – | – | – | – | – | – |
| 225 | – | – | – | – | – | – | – | – | – | – | – |
| 200 | – | – | – | – | – | – | – | – | – | – | – |
| 175 | – | – | – | – | – | – | – | – | – | – | – |
| 150 | – | – | – | – | – | – | – | – | – | – | – |
| 125 | – | – | – | – | – | – | – | – | – | – | + |
| 100 | – | – | – | – | – | – | – | – | – | – | + |
| 75 | – | – | – | – | – | – | – | – | – | – | + |
| 50 | – | – | – | – | – | – | – | – | + | + | + |
| 25 | – | – | – | – | – | – | + | + | + | + | + |
| 10 | – | – | – | – | – | – | + | + | + | + | + |
| 0 | – | – | – | – | – | – | + | + | + | + | + |

When the above-mentioned mixture of MIT and BIT was used, as well as an addition of IPBC, a synergy occurred.

Table XVIII shows the calculation of the synergy index. According to this, the lowest synergy index (0.80) for *Aspergillus niger* was at a mixture of, on the one hand, 99.0% by wt of MIT/BIT and, on the other hand, 1.0% by wt of IPBC.

TABLE XVIII

Calculation of the synergy index for *Aspergillus niger* at an incubation time of 72 h

| MIC at | | Total concentration | Concentration | | | | Synergy index |
|---|---|---|---|---|---|---|---|
| MIT/BIT concentration $Q_a$ (ppm) | IPBC concentration $Q_b$ (ppm) | BIT/MIT + IPBC $Q_a + Q_b$ (ppm) | MIT/BIT (% by wt) | IPBC (% by wt) | $Q_a/Q_A$ | $Q_b/Q_B$ | $Q_a/Q_A + Q_b/Q_B$ |
| 150 | 0 | 150 | 100.0 | 0.0 | 1.00 | 0.00 | 1.00 |
| 75 | 0.75 | 75.75 | 99.0 | 1.0 | 0.50 | 0.30 | 0.80 |
| 75 | 1 | 76 | 98,7 | 1.3 | 0.50 | 0.40 | 0.90 |

TABLE XVIII-continued

Calculation of the synergy index for *Aspergillus niger* at an incubation time of 72 h

| MIC at | | Total concentration | Concentration | | | | Synergy index |
|---|---|---|---|---|---|---|---|
| MIT/BIT concentration $Q_a$ (ppm) | IPBC concentration $Q_b$ (ppm) | BIT/MIT + IPBC $Q_a + Q_b$ (ppm) | MIT/BIT (% by wt) | IPBC (% by wt) | $Q_a/Q_A$ | $Q_b/Q_B$ | $Q_a/Q_A + Q_b/Q_B$ |
| 50 | 1.5 | 51.5 | 97.1 | 2.9 | 0.33 | 0.60 | 0.93 |
| 0 | 2.5 | 2.5 | 0.0 | 100.0 | 0.00 | 1.00 | 1.00 |

EXAMPLE 14

The synergy of an active substance mixture that contains IPBC in addition to MIT and BIT, against the microorganism *Penicillium funiculosum* is shown as in Example 1.

The test batches contained a Sabouraud maltose broth as a nutrient medium. The spore concentration was $10^6$ per mL. The incubation time was 72 h at 25° C. Each sample was incubated on an incubation shaker at 120 rpm.

Table XIX below shows the MIC values of the tested biocide compositions. The MIC value was 20 ppm when the MIT/BIT mixture alone was used, and 0.75 ppm when IPBC alone was used.

Table XX shows the calculation of the synergy index. According to this, the lowest synergy index (0.77) for *Penicillium funiculosum* was at a mixture of, on the one hand, 98.0% by wt of MIT/BIT and, on the other hand, 2.0% by wt of IPBC.

TABLE XIX

MIC values for *Penicillium funiculosum* at an incubation time of 72 h

| MIT/BIT concentration (ppm) | IPBC concentration (ppm) | | | | | | | | | |
|---|---|---|---|---|---|---|---|---|---|---|
| | 2 | 1.75 | 1.5 | 1.25 | 1 | 0.75 | 0.5 | 0.3 | 0.2 | 0.1 | 0 |
| 50 | − | − | − | − | − | − | − | − | − | − | − |
| 45 | − | − | − | − | − | − | − | − | − | − | − |
| 40 | − | − | − | − | − | − | − | − | − | − | − |
| 35 | − | − | − | − | − | − | − | − | − | − | − |
| 30 | − | − | − | − | − | − | − | − | − | − | − |
| 25 | − | − | − | − | − | − | − | − | − | − | − |
| 20 | − | − | − | − | − | − | − | − | − | − | − |
| 15 | − | − | − | − | − | − | − | − | − | − | + |
| 12.5 | − | − | − | − | − | − | − | − | − | + | + |
| 10 | − | − | − | − | − | − | − | − | − | + | + |
| 7.5 | − | − | − | − | − | − | − | + | + | + | + |
| 0 | − | − | − | − | − | − | + | + | + | + | + |

When the above-mentioned mixture of MIT and BIT was used, as well as an addition of IPBC, a synergy occurred.

TABLE XX

Calculation of the synergy index for *Penicillium funiculosum* at an incubation time of 72 h

| MIC at | | Total concentration | Concentration | | | | Synergy index |
|---|---|---|---|---|---|---|---|
| MIT/BIT concentration $Q_a$ (ppm) | IPBC concentration $Q_b$ (ppm) | MIT/BIT + IPBC (ppm) | MIT/BIT (% by wt) | IPBC (% by wt) | $Q_a/Q_A$ | $Q_b/Q_B$ | $Q_a/Q_A + Q_b/Q_B$ |
| 0 | 0.75 | 0.75 | 0.0 | 100.0 | 0.00 | 1.00 | 1.00 |
| 10 | 0.3 | 10.3 | 97.1 | 2.9 | 0.50 | 0.40 | 0.90 |
| 10 | 0.2 | 10.2 | 98.0 | 2.0 | 0.50 | 0.27 | 0.77 |
| 12.5 | 0.2 | 12.7 | 98.4 | 1.6 | 0.63 | 0.27 | 0.89 |
| 15 | 0.1 | 15.1 | 99.3 | 0.7 | 0.75 | 0.13 | 0.88 |
| 20 | 0 | 20 | 100.0 | 0.0 | 1.00 | 0.00 | 1.00 |

EXAMPLE 15

The synergy of an active substance mixture that contains 2-n-octylisothiazolin-3-one (OIT) in addition to MIT and BIT, against the microorganism *Aspergillus niger* is shown as in Example 1.

The test batches contained a Sabouraud maltose broth as a nutrient medium. The spore concentration was $10^6$ per mL. The incubation time was 72 h at 25° C. Each sample was incubated on an incubation shaker at 120 rpm.

Table XXI below shows the MIC values of the tested biocide compositions. The MIC value was 100 ppm when MIT/BIT alone was used, and 5 ppm when OIT alone was used.

TABLE XXI

MIC values for *Aspergillus niger* at an incubation time of 72 h

| MIT/BIT concentration (ppm) | OIT concentration (ppm) | | | | | | | |
|---|---|---|---|---|---|---|---|---|
| | 10 | 7.5 | 5 | 2.5 | 1 | 0.5 | 0.25 | 0 |
| 200 | − | − | − | − | − | − | − | − |
| 150 | − | − | − | − | − | − | − | − |
| 100 | − | − | − | − | − | − | − | − |
| 80 | − | − | − | − | − | − | − | + |
| 60 | − | − | − | − | − | + | + | + |
| 40 | − | − | − | − | + | + | + | + |
| 30 | − | − | − | − | + | + | + | + |
| 20 | − | − | − | + | + | + | + | + |
| 10 | − | − | − | + | + | + | + | + |
| 0 | − | − | − | + | + | + | + | + |

When the above-mentioned mixture of MIT and BIT was used, as well as an addition of OIT, a synergy occurred. Table XXII shows the calculation of the synergy index. According to this, the lowest synergy index (0.80) for *Aspergillus niger* was at a mixture of, on the one hand, 92.3% by wt of MIT/BIT and, on the other hand, 7.7% by wt of OIT, as well as at a mixture, of on the one hand, 98.4% by wt of MIT/BIT and, on the other hand, 1.6% by wt of OIT.

TABLE XXII

Calculation of the synergy index for *Aspergillus niger* at an incubation time of 72 h

| MIC at | | Total concentration | Concentration | | | | Synergy index |
|---|---|---|---|---|---|---|---|
| MIT/BIT concentration $Q_a$ (ppm) | OIT concentration $Q_b$ (ppm) | MIT/BIT + OIT (ppm) | MIT/BIT (% by wt) | OIT (% by wt) | $Q_a/Q_A$ | $Q_b/Q_B$ | $Q_a/Q_A + Q_b/Q_B$ |
| 0 | 5 | 5 | 0.0 | 100.0 | 0.00 | 1.00 | 1.00 |
| 30 | 2.5 | 32.5 | 92.3 | 7.7 | 0.30 | 0.50 | 0.80 |
| 40 | 2.5 | 42.5 | 94.1 | 5.9 | 0.40 | 0.50 | 0.90 |
| 60 | 1 | 61 | 98.4 | 1.6 | 0.60 | 0.20 | 0.80 |
| 80 | 0.5 | 80.5 | 99.4 | 0.6 | 0.80 | 0.10 | 0.90 |
| 100 | 0 | 100 | 100.0 | 0.0 | 1.00 | 0.00 | 1.00 |

EXAMPLE 16

The synergy of an active substance mixture that contains OIT in addition to MIT and BIT, against the microorganism *Penicillium funiculosum* is shown as in Example 1.

The test batches contained a Sabouraud maltose broth as a nutrient medium. The spore concentration was $10^6$ per mL. The incubation time was 72 h at 25° C. Each sample was incubated on an incubation shaker at 120 rpm.

Table XXIII below shows the MIC values of the tested biocide compositions. The MIC value was 50 ppm when MIT/BIT alone was used, and 5 ppm when OIT alone was used.

TABLE XXIII

MIC values for *Penicillium funiculosum* at an incubation time of 72 h

| MIT/BIT concentration (ppm) | OIT concentration (ppm) | | | | | |
|---|---|---|---|---|---|---|
| | 5 | 2.5 | 1 | 0.5 | 0.25 | 0 |
| 75 | − | − | − | − | − | − |
| 50 | − | − | − | − | − | − |
| 25 | − | − | − | − | − | + |
| 15 | − | − | − | + | + | + |
| 10 | − | − | + | + | + | + |
| 5 | − | − | + | + | + | + |
| 0 | − | + | + | + | + | + |

When the above-mentioned mixture of MIT and BIT was used, as well as an addition of OIT, a synergy occurred. Table XXIV shows the calculation of the synergy index. According to this, the lowest synergy index (0.50) for *Penicillium funiculosum* was at a mixture of 93.8% by wt of MIT/BIT, on the one hand, and 6.2% by wt of OIT, on the other hand.

TABLE XXIV

Calculation of the synergy index for *Penicillium funiculosum* at an incubation time of 72 h

| MIC at MIT/BIT concentration $Q_a$ (ppm) | MIC at OIT concentration $Q_b$ (ppm) | Total concentration MIT/BIT + OIT (ppm) | Concentration MIT/BIT (% by wt) | Concentration OIT (% by wt) | $Q_a/Q_A$ | $Q_b/Q_B$ | Synergy index $Q_a/Q_A + Q_b/Q_B$ |
|---|---|---|---|---|---|---|---|
| 0 | 5 | 5 | 0.0 | 100.0 | 0.00 | 1.00 | 1.00 |
| 5 | 2.5 | 7.5 | 66.7 | 33.3 | 0.10 | 0.50 | 0.60 |
| 10 | 2.5 | 12.5 | 80.0 | 20.0 | 0.20 | 0.50 | 0.70 |
| 15 | 2.5 | 17.5 | 85.7 | 14.3 | 0.30 | 0.50 | 0.80 |
| 15 | 1 | 16 | 93.8 | 6.2 | 0.30 | 0.20 | 0.50 |
| 25 | 1 | 26 | 96.2 | 3.8 | 0.50 | 0.20 | 0.70 |
| 25 | 0.5 | 25.5 | 98.0 | 2.0 | 0.50 | 0.10 | 0.60 |
| 25 | 0.25 | 25.25 | 99.0 | 1.0 | 0.50 | 0.05 | 0.55 |
| 50 | 0 | 50 | 100.0 | 0.0 | 1.00 | 0.00 | 1.00 |

EXAMPLE 17

The synergy of an active substance mixture that contains OIT in addition to MIT and BIT, against the microorganism *Saccharomyces cerevisiae* is shown as in Example 1.

The test batches contained a Sabouraud maltose broth as a nutrient medium. The cell density was $10^6$ cells/mL. The incubation time was 72 h at 25° C. Each sample was incubated on an incubation shaker at 120 rpm.

Table XXV below shows the MIC values of the tested biocide compositions. The MIC value was 40 ppm when MIT/BIT alone was used, and 5 ppm when OIT alone was used.

Table XXVI shows the calculation of the synergy index. According to this, the lowest synergy index (0.80) for *Saccharomyces cerevisiae* was at a mixture of 99.2% by wt of MIT/BIT on the one hand and 0.8% by wt of OIT on the other hand.

TABLE XXV

MIC values for *Saccharomyces cerevisiae* at an incubation time of 72 h

| MIT/BIT concentration (ppm) | OIT concentration (ppm) | | | | | | | | | |
|---|---|---|---|---|---|---|---|---|---|---|
| | 20 | 15 | 12.5 | 10 | 7.5 | 5 | 2.5 | 1 | 0.5 | 0.25 | 0 |
| 100 | − | − | − | − | − | − | − | − | − | − | − |
| 80 | − | − | − | − | − | − | − | − | − | − | − |
| 70 | − | − | − | − | − | − | − | − | − | − | − |
| 60 | − | − | − | − | − | − | − | − | − | − | − |
| 50 | − | − | − | − | − | − | − | − | − | − | − |
| 40 | − | − | − | − | − | − | − | − | − | − | − |
| 30 | − | − | − | − | − | − | − | − | − | − | + |
| 20 | − | − | − | − | − | − | − | + | + | + | + |
| 15 | − | − | − | − | − | − | + | + | + | + | + |
| 10 | − | − | − | − | − | − | + | + | + | + | + |
| 5 | − | − | − | − | − | − | + | + | + | + | + |
| 0 | − | − | − | − | − | − | + | + | + | + | + |

When the above-mentioned mixture of MIT and BIT was used, as well as an addition of OIT, a synergy occurred.

TABLE XXVI

Calculation of the synergy index for *Saccharomyces cerevisiae* at an incubation time of 72 h

| MIC at MIT/BIT concentration $Q_a$ (ppm) | MIC at OIT concentration $Q_b$ (ppm) | Total concentration MIT/BIT + OIT (ppm) | Concentration MIT/BIT (% by wt) | Concentration OIT (% by wt) | $Q_a/Q_A$ | $Q_b/Q_B$ | Synergy index $Q_a/Q_A + Q_b/Q_B$ |
|---|---|---|---|---|---|---|---|
| 0 | 5 | 5 | 0.0 | 100.0 | 0.00 | 1.00 | 1.00 |
| 30 | 1 | 31 | 96.8 | 3.2 | 0.75 | 0.20 | 0.95 |

TABLE XXVI-continued

Calculation of the synergy index for *Saccharomyces cerevisiae* at an incubation time of 72 h

| MIC at | | Total | Concentration | | | | |
|---|---|---|---|---|---|---|---|
| MIT/BIT concentration $Q_a$ (ppm) | OIT concentration $Q_b$ (ppm) | concentration MIT/BIT + OIT (ppm) | MIT/BIT (% by wt) | OIT (% by wt) | $Q_a/Q_A$ | $Q_b/Q_B$ | Synergy index $Q_a/Q_A + Q_b/Q_B$ |
| 30 | 0.5 | 30.5 | 98.4 | 1.6 | 0.75 | 0.10 | 0.85 |
| 30 | 0.25 | 30.25 | 99.2 | 0.8 | 0.75 | 0.05 | 0.80 |
| 40 | 0 | 40 | 100.0 | 0.0 | 1.00 | 0.00 | 1.00 |

EXAMPLE 18

The synergy of an active substance mixture that contains OIT in addition to MIT and BIT, against the microorganism *Pseudomonas aeruginosa* is shown as in Example 1.

The test batches contained a Müller-Hinton broth as a nutrient medium. The cell density was $10^6$ cells/mL. The incubation time was 144 h at 25° C. Each sample was incubated on an incubation shaker at 120 rpm.

Table XXVII below shows the MIC values of the tested biocide compositions. The MIC value was 30 ppm when MIT/BIT alone was used, and over 800 ppm when OIT alone was used.

Table XXVIII shows the calculation of the synergy index. According to this, the lowest synergy index (0.53) for *Pseudomonas aeruginosa* was at a mixture of 44.4% by wt of MIT/BIT, on the one hand, and 55.6% by wt of OIT, on the other hand.

TABLE XXVII

MIC values for *Pseudomonas aeruginosa* at an incubation time of 144 h

| MIT/BIT concentration (ppm) | OIT concentration (ppm) | | | | | | | | | | | | | |
|---|---|---|---|---|---|---|---|---|---|---|---|---|---|---|
| | 800 | 700 | 600 | 500 | 400 | 300 | 200 | 100 | 75 | 50 | 25 | 10 | 7.5 | 5 | 0 |
| 75 | − | − | − | − | − | − | − | − | − | − | − | − | − | − | − |
| 50 | − | − | − | − | − | − | − | − | − | − | − | − | − | − | − |
| 40 | − | − | − | − | − | − | − | − | − | − | − | − | − | − | − |
| 30 | − | − | − | − | − | − | − | − | − | − | − | − | − | − | − |
| 20 | − | − | − | − | − | − | − | − | − | − | − | + | + | + | + |
| 15 | − | − | − | − | − | − | − | + | + | + | + | + | + | + | + |
| 10 | − | − | − | − | − | + | + | + | + | + | + | + | + | + | + |
| 5 | − | − | + | + | + | + | + | + | + | + | + | + | + | + | + |
| 0 | + | + | + | + | + | + | + | + | + | + | + | + | + | + | + |

When the above-mentioned mixture of MIT and BIT was used, as well as an addition of OIT, a synergy occurred.

TABLE XXVIII

Calculation of the synergy index for *Pseudomonas aeruginosa* at an incubation time of 144 h

| MIC at | | Total | Concentration | | | | |
|---|---|---|---|---|---|---|---|
| MIT/BIT concentration $Q_a$ (ppm) | OIT concentration $Q_b$ (ppm) | concentration MIT/BIT + OIT (ppm) | MIT/BIT (% by wt) | OIT (% by wt) | $Q_a/Q_A$ | $Q_b/Q_B$ | Synergy index $Q_a/Q_A + Q_b/Q_B$ |
| 0 | 900 | 900 | 0.0 | 100.0 | 0.00 | 1.00 | 1.00 |
| 5 | 700 | 705 | 0.7 | 99.3 | 0.13 | 0.78 | 0.90 |
| 10 | 600 | 610 | 1.6 | 98.4 | 0.25 | 0.67 | 0.92 |
| 10 | 500 | 510 | 2.0 | 98.0 | 0.25 | 0.56 | 0.81 |
| 10 | 400 | 410 | 2.4 | 97.6 | 0.25 | 0.44 | 0.69 |
| 15 | 300 | 315 | 4.8 | 95.2 | 0.38 | 0.33 | 0.71 |
| 15 | 200 | 215 | 7.0 | 93.0 | 0.38 | 0.22 | 0.60 |
| 20 | 100 | 120 | 16.7 | 83.3 | 0.50 | 0.11 | 0.61 |
| 20 | 75 | 95 | 21.1 | 78.9 | 0.50 | 0.08 | 0.58 |

TABLE XXVIII-continued

Calculation of the synergy index for *Pseudomonas aeruginosa* at an incubation time of 144 h

| MIC at | | Total | Concentration | | | | |
|---|---|---|---|---|---|---|---|
| MIT/BIT | OIT | concentration | | | | | |
| concentration $Q_a$ (ppm) | concentration $Q_b$ (ppm) | MIT/BIT + OIT (ppm) | MIT/BIT (% by wt) | OIT (% by wt) | $Q_a/Q_A$ | $Q_b/Q_B$ | Synergy index $Q_a/Q_A + Q_b/Q_B$ |
| 20 | 50 | 70 | 28.6 | 71.4 | 0.50 | 0.06 | 0.56 |
| 20 | 25 | 45 | 44.4 | 55.6 | 0.50 | 0.03 | 0.53 |
| 40 | 0 | 40 | 100.0 | 0.0 | 1.00 | 0.00 | 1.00 |

EXAMPLE 19

The synergy of an active substance mixture that contains formaldehyde (HCHO) in addition to MIT and BIT, against the microorganism *Escherichia coli* is shown as in Example 1.

The test batches contained a Müller-Hinton broth as a nutrient medium. The cell density was $10^6$ cells/mL. The incubation time was 48 b at 25° C. Each sample was incubated on an incubation shaker at 120 rpm.

Table XXIX below shows the MIC values of the tested biocide compositions. The MIC value was 25 ppm when MIT/BIT alone was used, and 300 ppm when HCHO alone was used.

Table XXX shows the calculation of the synergy index. According to this, the lowest synergy index (0.77) for *Escherichia coli* was at a mixture of 23.1% by wt of MIT/BIT on the one hand and 76.9% by wt of HCHO on the other hand.

TABLE XXIX

MIC values for *Escherichia coli* at an incubation time of 48 h

| MIT/BIT concentration | HCHO concentration (ppm) | | | | | | | | | | | |
|---|---|---|---|---|---|---|---|---|---|---|---|---|
| (ppm) | 1000 | 900 | 800 | 700 | 600 | 500 | 400 | 300 | 200 | 100 | 50 | 0 |
| 45 | − | − | − | − | − | − | − | − | − | − | − | − |
| 40 | − | − | − | − | − | − | − | − | − | − | − | − |
| 35 | − | − | − | − | − | − | − | − | − | − | − | − |
| 30 | − | − | − | − | − | − | − | − | − | − | − | − |
| 25 | − | − | − | − | − | − | − | − | − | − | − | − |
| 20 | − | − | − | − | − | − | − | − | − | − | − | + |
| 15 | − | − | − | − | − | − | − | − | − | − | − | + |
| 12.5 | − | − | − | − | − | − | − | − | − | − | + | + |
| 10 | − | − | − | − | − | − | − | − | − | + | + | + |
| 7.5 | − | − | − | − | − | − | − | − | − | + | + | + |
| 5 | − | − | − | − | − | − | − | − | + | + | + | + |
| 0 | − | − | − | − | − | − | − | − | + | + | + | + |

When the above-mentioned mixture of MIT and BIT was used, as well as an addition of HCHO, a synergy occurred.

TABLE XXX

Calculation of the synergy index for *Escherichia coli* at an incubation time of 48 h

| MIC at | | Total | Concentration | | | | |
|---|---|---|---|---|---|---|---|
| MIT/BIT | HCHO | concentration | | | | | |
| concentration $Q_a$ (ppm) | concentration $Q_b$ (ppm) | MIT/BIT + HCHO (ppm) | MIT/BIT (% by wt) | HCHO (% by wt) | $Q_a/Q_A$ | $Q_b/Q_B$ | Synergy index $Q_a/Q_A + Q_b/Q_B$ |
| 0 | 300 | 300 | 0.0 | 100.0 | 0.00 | 1.00 | 1.00 |
| 7.5 | 200 | 207.5 | 3.6 | 96.4 | 0.30 | 0.67 | 0.97 |
| 12.5 | 100 | 112.5 | 11.1 | 88.9 | 0.50 | 0.33 | 0.83 |

TABLE XXX-continued

Calculation of the synergy index for *Escherichia coli* at an incubation time of 48 h

| MIC at | | Total | Concentration | | | | |
|---|---|---|---|---|---|---|---|
| MIT/BIT concentration $Q_a$ (ppm) | HCHO concentration $Q_b$ (ppm) | concentration MIT/BIT + HCHO (ppm) | MIT/BIT (% by wt) | HCHO (% by wt) | $Q_a/Q_A$ | $Q_b/Q_B$ | Synergy index $Q_a/Q_A + Q_b/Q_B$ |
| 15 | 50 | 65 | 23.1 | 76.9 | 0.60 | 0.17 | 0.77 |
| 25 | 0 | 25 | 100.0 | 0.0 | 1.00 | 0.00 | 1.00 |

EXAMPLE 20

The synergy of an active substance mixture that contains HCHO in addition to MIT and BIT, against the microorganism *Pseudomonas aeruginosa* is shown as in Example 1.

The test batches contained a Müller-Hinton broth as a nutrient medium. The cell density was $10^6$ cells/mL. The incubation time was 48 h at 25° C. Each sample was incubated on an incubation shaker at 120 rpm.

Table XXXI below shows the MIC values of the tested biocide compositions. The MIC value was 30 ppm when MIT/BIT alone was used, and 300 ppm when HCHO alone was used.

According to this, the lowest synergy index (0.75) for *Pseudomonas aeruginosa* was at a mixture of 11.1% by wt of MIT/BIT, on the one hand, and 88.9% by wt of HCHO, on the other hand.

TABLE XXXI

MIC values for *Pseudomonas aeruginosa* at an incubation time of 48 h

| MIT/BIT concentration (ppm) | HCHO concentration (ppm) | | | | | | | | | | |
|---|---|---|---|---|---|---|---|---|---|---|---|
| | 1000 | 900 | 800 | 700 | 600 | 500 | 400 | 300 | 200 | 100 | 50 | 0 |
| 45 | − | − | − | − | − | − | − | − | − | − | − | − |
| 40 | − | − | − | − | − | − | − | − | − | − | − | − |
| 35 | − | − | − | − | − | − | − | − | − | − | − | − |
| 30 | − | − | − | − | − | − | − | − | − | − | − | − |
| 25 | − | − | − | − | − | − | − | − | − | − | − | + |
| 20 | − | − | − | − | − | − | − | − | − | − | − | + |
| 15 | − | − | − | − | − | − | − | − | − | − | + | + |
| 12.5 | − | − | − | − | − | − | − | − | − | − | + | + |
| 10 | − | − | − | − | − | − | − | − | − | + | + | + |
| 7.5 | − | − | − | − | − | − | − | − | − | + | + | + |
| 5 | − | − | − | − | − | − | − | − | + | + | + | + |
| 0 | − | − | − | − | − | − | − | − | + | + | + | + |

When the above-mentioned mixture of MIT and BIT was used, as well as an addition of HCHO, a synergy occurred. Table XXXII shows the calculation of the synergy index.

TABLE XXXII

Calculation of the synergy index for *Pseudomonas aeruginosa* at an incubation time of 48 h

| MIC at | | Total | Concentration | | | | |
|---|---|---|---|---|---|---|---|
| MIT/BIT concentration $Q_a$ (ppm) | HCHO concentration $Q_b$ (ppm) | concentration MIT/BIT + HCHO (ppm) | MIT/BIT (% by wt) | HCHO (% by wt) | $Q_a/Q_A$ | $Q_b/Q_B$ | Synergy index $Q_a/Q_A + Q_b/Q_B$ |
| 0 | 300 | 300 | 0.0 | 100.0 | 0.00 | 1.00 | 1.00 |
| 7.5 | 200 | 207.5 | 3.6 | 96.4 | 0.25 | 0.67 | 0.92 |
| 12.5 | 100 | 112.5 | 11.1 | 88.9 | 0.42 | 0.33 | 0.75 |
| 15 | 100 | 115 | 13.0 | 87.0 | 0.50 | 0.33 | 0.83 |
| 20 | 50 | 70 | 28.6 | 71.4 | 0.67 | 0.17 | 0.83 |
| 30 | 0 | 30 | 100.0 | 0.0 | 1.00 | 0.00 | 1.00 |

EXAMPLE 21

The synergy of an active substance that contains 2-bromo-2-nitropropane-1,3-diol (BNPD) in addition to MIT and BIT, against the microorganism *Penicillium funiculosum* is shown as in Example 1.

The test batches contained a Sabouraud maltose broth as a nutrient medium. The spore concentration was $10^6$ per mL. The incubation time was 72 h at 25° C. Each sample was incubated on an incubation shaker at 120 rpm.

Table XXXIII below shows the MIC values of the tested biocide compositions. The MIC value was 25 ppm when MIT/BIT alone was used, and 600 ppm when BNPD alone was used.

TABLE XXXIII

MIC values for *Penicillium funiculosum* at an incubation time of 72 h

| MIT/BIT concentration | BNPD concentration (ppm) | | | | | | | | | | |
|---|---|---|---|---|---|---|---|---|---|---|---|
| (ppm) | 1000 | 800 | 600 | 400 | 300 | 200 | 150 | 100 | 50 | 25 | 0 |
| 50 | − | − | − | − | − | − | − | − | − | − | − |
| 45 | − | − | − | − | − | − | − | − | − | − | − |
| 40 | − | − | − | − | − | − | − | − | − | − | − |
| 35 | − | − | − | − | − | − | − | − | − | − | − |
| 30 | − | − | − | − | − | − | − | − | − | − | − |
| 25 | − | − | − | − | − | − | − | − | − | − | − |
| 20 | − | − | − | − | − | − | − | − | − | − | + |
| 15 | − | − | − | − | − | − | − | − | − | + | + |
| 12.5 | − | − | − | − | − | − | − | + | + | + | + |
| 10 | − | − | − | − | − | − | + | + | + | + | + |
| 7.5 | − | − | − | − | − | + | + | + | + | + | + |
| 0 | − | − | − | + | + | + | + | + | + | + | + |

When the above-mentioned mixture of MIT and BIT was used, as well as an addition of BNPD, a synergy occurred. Table XXXIV shows the calculation of the synergy index. According to this, the lowest synergy index (0.67) for *Penicillium funiculosum* was at a mixture of, on the one hand, 11.1% by wt of MIT/BIT and, on the other hand, 88.9% by wt of BNPD.

TABLE XXXIV

Calculation of the synergy index for *Penicillium funiculosum* at an incubation time of 72 h

| MIC at | | Total | Concentration | | | | Synergy index |
|---|---|---|---|---|---|---|---|
| MIT/BIT concentration $Q_a$ (ppm) | BNPD concentration $Q_b$ (ppm) | concentration MIT/BIT + BNPD (ppm) | MIT/BIT (% by wt) | BNPD (% by wt) | $Q_a/Q_A$ | $Q_b/Q_B$ | $Q_a/Q_A + Q_b/Q_B$ |
| 25 | 0 | 25 | 100.0 | 0.0 | 1.00 | 0.00 | 1.00 |
| 20 | 25 | 45 | 44.4 | 55.6 | 0.80 | 0.04 | 0.84 |
| 20 | 50 | 70 | 28.6 | 71.4 | 0.80 | 0.08 | 0.88 |
| 15 | 50 | 65 | 23.1 | 76.9 | 0.60 | 0.08 | 0.68 |
| 15 | 1oo | 115 | 13.0 | 87.0 | 0.60 | 0.17 | 0.77 |
| 12.5 | 100 | 112.5 | 11.1 | 88.9 | 0.50 | 0.17 | 0.67 |
| 12.5 | 150 | 162.5 | 7.7 | 92.3 | 0.50 | 0.25 | 0.75 |
| 12.5 | 200 | 212.5 | 5.9 | 94.1 | 0.50 | 0.33 | 0.83 |
| 10 | 200 | 210 | 4.8 | 95.2 | 0.40 | 0.33 | 0.73 |
| 7.5 | 300 | 307.5 | 2.4 | 97.6 | 0.30 | 0.50 | 0.80 |
| 7.5 | 400 | 407.5 | 1.8 | 98.2 | 0.30 | 0.67 | 0.97 |
| 0 | 600 | 600 | 0.0 | 100.0 | 0.00 | 1.00 | 1.00 |

What is claimed is:

1. A biocide composition comprising at least two active biocidal substances, selected from the group consisting of 2-methylisothiazolin-3-one and 1,2-benzisothiazolin-3-one, said biocide composition being free of any 5-chloro-2-methylisothiazolin-3-one.

2. A biocide composition according to claim 1, wherein 2-methylisothiazolin-3-one and 1,2-benzisothiazolin-3-one are present in a weight ratio of 50:1 to 1:50.

3. A biocide composition according to claim 2, wherein 2-methylisothiazolin-3-one and 1,2-benzisothiazolin-3-one are present in a weight ratio of 15:1 to 1:8.

4. A biocide composition as in any of the preceding claims, in which said composition contains 2-methylisothiazolin-3-one and 1,2-benzisothiazolin-3-one in a total concentration of 1 to 20% by wt relative to the total biocide composition.

5. A biocide composition as in claim 1, wherein said composition contains a polar and/or nonpolar liquid medium.

6. A biocide composition according to claim 5, wherein said composition contains as a polar liquid medium, water, an aliphatic alcohol having 1 to 4 carbon atoms, a glycol, a glycol ether, a glycol ester, a polyethylene glycol, a polypropylene glycol, N, N-dimethylformamide, or a mixture of such substances.

7. A biocide composition according to claim 6, wherein the polar liquid medium is water and said composition has a pH of 7 to 9.

8. A biocide composition according to claim 5, containing as a nonpolar liquid medium xylene and/or toluene.

9. A biocide composition according to claim 1, containing 3-iodo-2-propinyl-N-butyl carbamate as an active biocidal substance.

10. A biocide composition according to claim 9, wherein the weight ratio of the combination of 2-methylisothiazolin-3-one and 1,2-benzisothiazolin-3-one to 3-iodo-2-propinyl-N-butyl carbamate ranges from 1:10 to 100:1.

11. A biocide composition according to claim 1 containing 2-n-octylisothiazolin-3-one as an active biocidal substance.

12. A biocide composition according to claim 11, wherein the weight ratio of the combination of 2-methylisothiazolin-3-one and 1,2-benzisothiazolin-3-one to 2-n-octylisothiazolin-3-one ranges from 1:10 to 100:1.

13. A biocide composition according to claim 1 containing formaldehyde or a formaldehyde source material as an active biocidal substance.

14. A biocide composition according to claim 13, wherein the weight ratio of the combination of 2-methylisothiazolin-3-one and 1,2-benzisothiazolin-3-one to the formaldehyde source material ranges from 1:100 to 10:1.

15. A biocide composition according to claim 1 additionally containing 2-bromo-2-nitropropane-1,3-diol as an active biocidal substance.

16. A biocide composition according to claim 15, wherein the weight ratio of the combination of 2-methylisothiazolin-3-one and 1,2-benzisothiazolin-3-one to 2-bromo-2-nitropropane-1,3-diol ranges from 1:10 to 10:1.

17. A biocide composition according to claim 9 containing 2-methylisothiazolin-3-one and 1,2-benzisothiazolin-3-one in a weight ratio of 1:1.

18. A method for controlling harmful microorganisms which comprises applying to said harmful microorganisms a biocide composition, said composition comprising:

1) 2-methylisothiazolin-3-one; and
2) 1,2-benzisothiazolin-3-one and;
3) said biocide composition being free of 5-chloro-2-methylisothiazolin-3-one.

\* \* \* \* \*